(12) United States Patent
Blackburn et al.

(10) Patent No.: US 8,625,744 B2
(45) Date of Patent: Jan. 7, 2014

(54) APPARATUS AND METHODS FOR REAL-TIME DETECTION OF EXPLOSIVES DEVICES

(75) Inventors: Brandon W. Blackburn, Idaho Falls, ID (US); Alan W. Hunt, Pocatello, ID (US); David L. Chichester, Idaho Falls, ID (US)

(73) Assignees: U.S. Department of Energy, Washington, DC (US); Raytheon Company, Waltham, MA (US)

( * ) Notice: Subject to any disclaimer, the term of this patent is extended or adjusted under 35 U.S.C. 154(b) by 900 days.

(21) Appl. No.: 12/622,813

(22) Filed: Nov. 20, 2009

(65) Prior Publication Data

US 2011/0121979 A1    May 26, 2011

(51) Int. Cl.
*G01N 23/22*    (2006.01)

(52) U.S. Cl.
USPC ............... 378/210; 378/57; 210/310

(58) Field of Classification Search
USPC .............. 378/57, 88, 210; 250/306, 307, 310, 250/399
See application file for complete search history.

(56) References Cited

U.S. PATENT DOCUMENTS

| | | | |
|---|---|---|---|
| 4,980,901 A * | 12/1990 | Miller | 378/45 |
| 5,524,133 A | 6/1996 | Neale et al. | 378/53 |
| 6,155,155 A | 12/2000 | Moshier | 89/1.13 |
| 6,567,496 B1 * | 5/2003 | Sychev | 378/57 |
| 6,584,879 B2 | 7/2003 | Gorman | 89/1.11 |
| 6,678,351 B1 | 1/2004 | Perry et al. | 378/119 |
| 7,286,638 B2 | 10/2007 | Ledoux et al. | 378/88 |
| 2003/0128804 A1 * | 7/2003 | Poteet et al. | 378/44 |
| 2007/0019788 A1 * | 1/2007 | Ledoux et al. | 378/88 |
| 2007/0098142 A1 * | 5/2007 | Rothschild et al. | 378/57 |
| 2009/0190719 A1 * | 7/2009 | Barschdorf et al. | 378/137 |
| 2011/0129066 A1 * | 6/2011 | Statham et al. | 378/88 |
| 2012/0037811 A1 * | 2/2012 | Dunn | 250/391 |

FOREIGN PATENT DOCUMENTS

WO   WO 2007/127598   11/2007 ............. G01M 3/00

* cited by examiner

*Primary Examiner* — Glen Kao
(74) *Attorney, Agent, or Firm* — Cantor Colburn LLP

(57) ABSTRACT

The present disclosure relates, according to some embodiments, to apparatus, devices, systems, and/or methods for real-time detection of a concealed or camouflaged explosive device (e.g., EFPs and IEDs) from a safe stand-off distance. Apparatus, system and/or methods of the disclosure may also be operable to identify and/or spatially locate and/or detect an explosive device. An apparatus or system may comprise an x-ray generator that generates high-energy x-rays and/or electrons operable to contact and activate a metal comprised in an explosive device from a stand-off distance; and a detector operable to detect activation of the metal. Identifying an explosive device may comprise detecting characteristic radiation signatures emitted by metals specific to an EFP, an IED or a landmine. Apparatus and systems of the disclosure may be mounted on vehicles and methods of the disclosure may be performed while moving in the vehicle and from a safe stand-off distance.

22 Claims, 3 Drawing Sheets

APPARATUS AND METHODS FOR REAL-TIME DETECTION OF EXPLOSIVES DEVICES

GOVERNMENT LICENSE RIGHTS

This invention was made with government support under Contract Number DE-AC07-051D14517 awarded by the United States Department of Energy. The government has certain rights in the invention.

FIELD OF THE DISCLOSURE

The present disclosure relates, in some embodiments, to apparatus, devices, systems, and methods for remotely detecting and spatially locating concealed or camouflaged explosive devices (e.g., an explosively formed penetrator (EFP), an improvised explosive device (IED)), in real-time and from safe stand-off distances.

BACKGROUND OF THE DISCLOSURE

Improvised Explosive Devices (IEDs) and Explosively Formed Penetrators (EFPs) have accounted for a large number of combat casualties. Despite focused efforts on armor development, Mine Resistant Ambush Protected (MRAP) vehicles and other armored vehicles still cannot defend against these threats. The lethality of EFPs comes from the arrangement of a concave copper cone, called the liner, which transforms into a forceful plasma jet of molten metal which easily perforates steel armor.

Presently there are no available devices or methods for remotely identifying and locating explosive devices, such as EFPs and IEDs, at safe stand-off distances and in real time. Present technology is limited to detecting explosives concealed in luggage where the target luggage is passed through a scanner thereby bringing the concealed explosive device in close proximity of a detector. However, in combat situations it is necessary to detect explosive devices at safe stand-off distances and with rapidity to enable a convoy vehicle to instantly change course to avoid contact with the concealed explosive device.

SUMMARY

Accordingly, a need has arisen for improved apparatus, devices, systems, and methods for detecting concealed explosive devices remotely and in real-time and to identify and spatially locate such devices.

The present disclosure relates, according to some embodiments, to apparatus, devices, systems and/or methods for detecting concealed explosive devices (including EFPs, IEPs and landmines) in real-time and remotely from safe stand-off distances. In some embodiments, apparatus, devices, systems and/or methods according to the disclosure may be further operable to identify the spatial location and the nature of concealed explosive devices.

In some embodiments, an apparatus, a device, a system or a method of the disclosure may be operable to detect specific metals that are comprised in explosive devices (e.g., copper contained in an EFP) and may comprise one or more components including a high energy x-ray generator operable to generate high-energy x-rays and/or high energy electrons that may penetrate an explosive device and activate a metal embedded therein; a radiation detector; a radiation analyzer; and an output module. In some embodiments, apparatus, devices, systems, and methods of the disclosure may be placed in or on a vehicle and may be operable to detect concealed explosive devices from stand-off distances in real-time while moving at convoy speeds.

This summary contains only a limited number of examples of various embodiments and features of the present disclosure. For a better understanding of the disclosure and its advantages, reference may be made to the description of exemplary embodiments that follows.

BRIEF DESCRIPTION OF THE DRAWINGS

Some embodiments of the disclosure may be understood by referring, in part, to the present disclosure and the accompanying drawings, wherein.

DETAILED DESCRIPTION

The present disclosure relates, in some embodiments, to apparatus, devices, systems and methods for locating and identifying concealed explosive devices such as IEDs, EFPs and landmines that are increasingly being used in combat zones as well as in civilian areas.

In some embodiments, an apparatus, a device and/or a system of the disclosure may be operable to rapidly scan an area suspected of containing a concealed explosive device from a safe stand-off distance, rapidly detect, identify and spatially locate the explosive device in real-time and immediately provide the information gathered to an operator. In some embodiments, an apparatus, a device and/or a system of the disclosure may be mounted onto vehicles such as military convoy vehicles or a personal vehicle and may be operable to rapidly detect, identify and locate a concealed explosive device in real time, while travelling at a normal operational speed of the vehicle, from a safe stand-off distance to avoid driving over and setting off the detonation of such a device.

An apparatus, device, system and/or method of the present disclosure may be operable to detect and identify an explosive device from a safe stand-off distance of about 10 meters (10 m) to about 100 meters (100 m) to provide sufficient protection and time for changing course away from the explosive device.

Explosive devices typically contain a few kilograms of metal. EFPs for example are designed to have a copper liner arranged as a concave copper cone that upon detonation transforms into a lethal forceful plasma jet of molten metal that can perforate through steel armored military vehicles that are in its range. Some EFPs may comprise copper alloys such as brass. IEDs and land mines may comprise metals or alloys such as iron, steel and/or aluminum.

Teachings of the present disclosure, according to some embodiments, may be used to identify EFPs based on generation of unique radiation signatures of copper resulting from the activation of copper in the liner. For example, high energy x-rays and/or high energy electrons may be used to activate the copper (or brass) liner material in an EFP thereby generating radiation from copper which may be detected and imaged. Radiation emitted by copper produces a radiation signature that is specific for copper and may comprise a 511 keV annihilation photon produced by positron decay of $^{62}$Cu and $^{64}$Cu. In some embodiments, radiation signatures of copper may comprise peaks in detector pulse height spectra at 875 keV and 1173 keV.

Imaging an IED, according to some embodiments of the disclosure, may comprise detecting radiation signatures of iron. In some embodiments, a radiation signature of iron may comprise a peak at 378 keV. Imaging may be achieved by use of Compton coincidence imaging and coded aperture techniques to spatially resolve the location of the source of detected radiations of copper, iron and/or other metals or alloys comprised in an explosive of interest.

Figure 1:
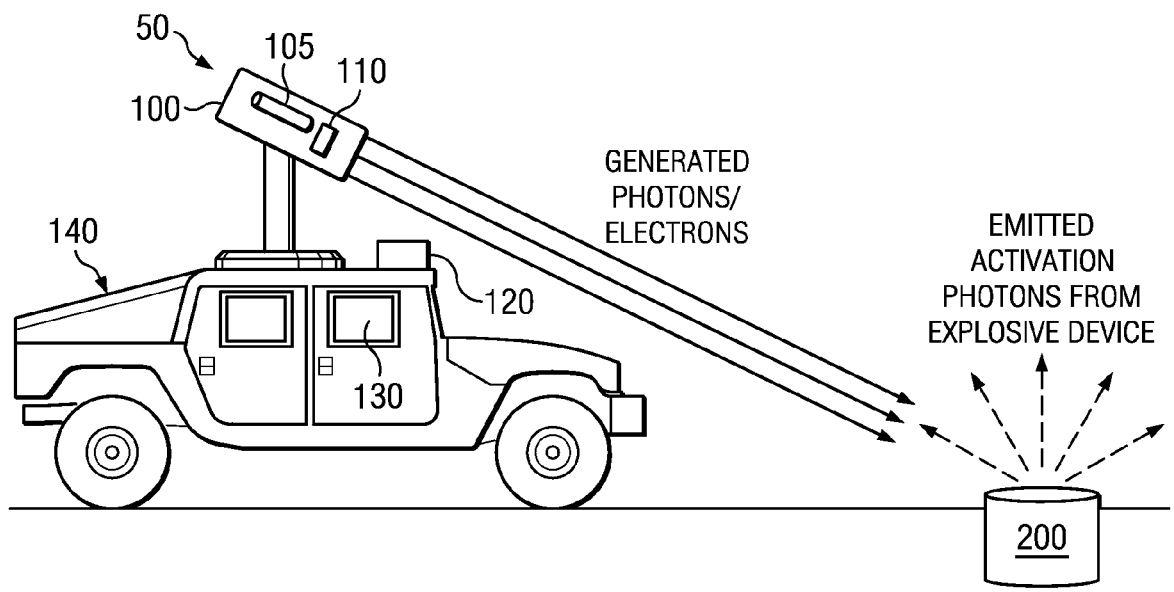
FIG. 1 is a schematic drawing showing a system and associated apparatus operable to detect remote and concealed explosive devices, according to a specific example embodiment of the disclosure.
Figure 2:
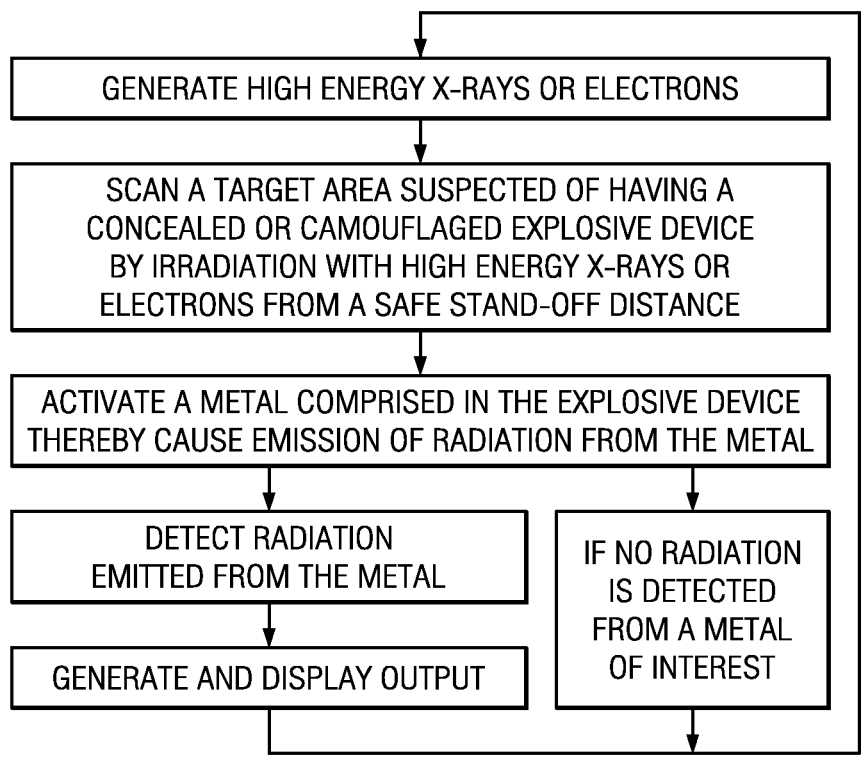
FIG. 2 is a block diagram showing a method for detecting remote and concealed explosive devices, according to a specific example embodiment of the disclosure.
Figure 3:
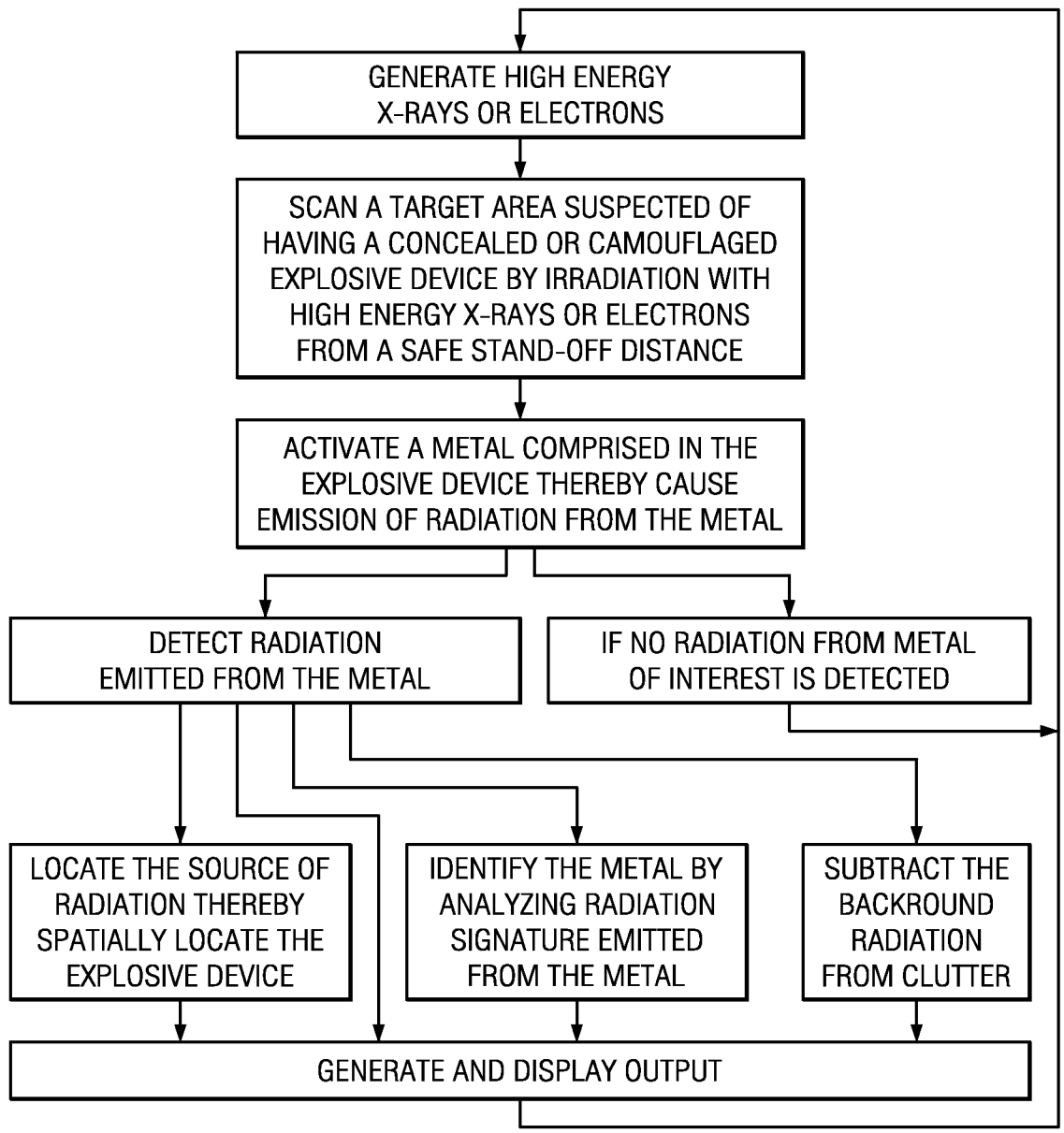
FIG. 3 is a block diagram showing a method for detecting remote and concealed explosive devices, according to another specific example embodiment of the disclosure.

Preferred embodiments of the disclosure and its advantages may be best understood by reference to FIGS. 1-3.

An exemplary system 50 of the disclosure, operable to identify an explosive device, is illustrated in FIG. 1. In some embodiments system 50 may be referred to as an apparatus and/or device and may comprise an array of devices. System 50 may comprise a high voltage x-ray generator 100 that is operable to generate high energy x-rays and/or high energy electrons that may range from about 10 MeV to about 20 MeV.

High energy x-ray generator 100 may comprise an electron accelerator 105 operable to generate high energy electrons, x-rays or Bremsstrahlung pulses. Electron accelerator 105 may be a compact electron accelerator, a high voltage electron accelerator, an X-ray band linacs system, an x-ray accelerator, a medical linac system and/or a laser.

High-energy x-rays or electrons produce short-lived radiations upon contact with a metal, which may be collected, analyzed and imaged in real-time to identify explosive devices even when buried or camouflaged. The high energy x-rays or electrons used to activate metals of interest (i.e., metals contained in explosive devices), do not generate long-lived radioactive elements nor do they generate competing signatures in elements such as iron, silicon, hydrogen, oxygen, nitrogen and carbon which make up the bulk of benign materials found alongside roads or highways.

In some embodiments, x-ray generator 100 may further comprise a scanner component 110 that allows the high energy x-rays and/or electrons generated by x-ray generator 100 to be swept along an area that is suspected to contain an explosive device 200. A scanner 110 may use electric and magnetic fields to steer or direct an electron accelerator beam in a direction of interest.

A scanner component 110 may comprise a means to rotate and focus a beam of high energy x-rays and/or electrons onto areas of a target suspected of having a concealed or camouflaged explosive device for a given amount of time. Focusing a beam of high energy x-rays and/or electrons onto areas of a target for a pre-determined amount of time allows the high energy x-rays and/or electrons to bombard, penetrate and activate any metal of interest that may be present in the target area. Activation of a metal in any concealed explosive device by the high-energy x-rays and/or electrons produces radiation that may be captured, detected and analyzed.

System 50 may further comprise a detector 120 operable to capture and/or detect radiation generated from a metal contained in an explosive device 200 following activation by high energy x-rays. A detector 120 may comprise a radiation detector. A detector 120 may be operable to image detected radiation. A detector 120 may be further operable to spatially locate the source of radiation using Compton imaging and coded aperture techniques.

In some embodiments, a detector 120 may comprise components or modules that may be operable to identify specific radiation signatures generated by the activation of a metal of interest. For example, detector components or modules may be operable to compare the radiation detected with a databank of radiation signatures of different metals and/or other components (such as material making up roads and/or other benign clutter that may be found typically in an area where an explosive device may be concealed) and thereby may be able to identify a metal or other compound of interest. In some embodiments, detector 120 may comprise a computer memory populated with a database of radiation signatures of metals and other materials of interest. Accordingly, a detector 120 may be operable to identify the material responsible for generating radiation (e.g., a metal contained in a concealed explosive device).

In one example, simulations and experimentation using an example apparatus of the disclosure used 15 MeV and 22 MeV endpoint Bremsstrahlung x-ray sources to activate a 6.35 mm thick copper disk having a radius of about 7.62 cm. These high energy x-rays produced activity levels in excess of hundreds of microcuries (μCi) from the copper disc within several seconds. X-rays of even higher energies may be generated using electron accelerators with accelerated currents (e.g., X-band linacs) to reduce the response time for generation of radiation. These experiments also provide radiation signatures for metals of interest such as copper.

Similar experiments may be performed with other metals or alloys of interest (i.e., metals and alloys that may be present in other explosive devices), such as but not limited to iron, steel, brass and/or aluminum to generate radiation signatures characteristic of these materials and to evaluate and adjust the response time for obtaining signals of interest.

Other materials for which radiation signatures of interest may be generated by the experiments outlined above include benign clutter material such as sand, tar, carbon, silicon, material used in roads and material generally found in a typical area where explosives may be buried. While these materials may produce very little competing signals, their radiation signature (formed in response to activation by the inspecting high energy x-rays) allows a practitioner to distinguish and/or identify them since these materials are ubiquitous in real-world situations. In a combat search scenario for explosive devices, it may be necessary to distinguish radiation signals generated by a metal of interest originating from an explosive device from a diffuse background of radiation signals which may originate from other benign materials.

Following the collection of radiation signatures of metals, alloys (or other materials) comprised in explosive devices and materials present in benign clutter, a comprehensive database (or databank) may be populated with these radiation signatures. Such a database may be operably connected (or interfaced) with detector 120 to enable the identification of different materials based on radiation signatures generated. The quantity and spectral information of various emission signatures may be analyzed by a detector component as a function of the nature of the metal or alloy, and/or the irradiation time, and/or distance from the x-ray source and x-ray energy for obtaining data relating to identity of an explosive device, time of response, and spatial location and/or safe stand-off distance information respectively. This data may also be input into simulation codes being utilized for a detector system (e.g., a passive Stand-off Radiation Detection System (SORDS)), to predict acquisition times and image quality that may be obtained by system 50 of the disclosure.

In one example, a passive SORDS imager designed for operation with gamma energies from 40 to 3000 keV was used to analyze radiation signatures from copper in a surrogate EFP. Characteristic copper radiation signatures as set forth above were observed. Although the specific x-ray energies (γ,n) chosen to activate a surrogate EFP liner produces very few radiations in clutter material such as silicon, hydrogen, oxygen, nitrogen and carbon, imaging radiation emitted by clutter materials is nevertheless important to identify true threats which may show up as point sources. This may confer detector components an ability of to distinguish point sources bearing radiation signatures characteristic of metals of interest from diffuse radiation background that may be generated by ground clutter.

Accordingly, in some embodiments, detector 120 may contain components or modules operable to subtract radiation generated by benign clutter located in a target area from the entire radiation signal detected by the detector, thereby allowing the detection of point sources of a metal of interest.

Typically, a detector 120 may be operable to rapidly detect and/or rapidly identify a metal of interest and provide such information rapidly to an operator and/or an output module 130. Accordingly, a detector 120 may comprise one or more of the following non-limiting components or modules including: a sensor, a Compton imager, a stand-off radiation detection system (SORDS), an imager with a NaI-based coded aperture, a photon detector, a Geiger counter, a scintillation counter, a data collection module, a data processing module, a module to detect and subtract background radiation from the surrounding area, a module operable to store radiation signatures of different metals (e.g., database), an identification module, an output module, an alarm module and any combinations thereof.

Another component of system 50 may be an output module 130 which may be operable to interface with detector 120 and may be further operable to display and/or transmit information relating to the radiation detected by detector 120. Output module 130 may be connected to the detector 120 to receive raw data which may be processed in the module prior to display. Information displayed may include detector pulse height spectra, suspected source isotopes of peak signatures, images of spatially resolved radiation sources drawn from Compton coincidence and coded aperture reconstructions and combinations thereof. An output module 130 may comprise a screen that may alert an operator or a computer of the presence of an explosive device based on a set of characteristics associated with an explosive device such as isotopic compositions, intensity of radiation from activated material, and apparent spatial distribution of radiation source. For example, upon receipt of data from detector 120 of specific γ rays that may correspond to a radioactive copper signal, output module 130 may conduct an algorithm to verify that the source of the γ rays is from the same spatial location.

In some embodiments, an alarm component (not expressly depicted) of output module 130 may be activated providing an audible alarm alerting an operator to change course, for example, of a convoy vehicle, following detection of an explosive device in a target area. In some embodiments, an output module display may be on the windscreen of a convoy vehicle showing in real-time an identified target concealing an explosive device.

Suitable electron accelerators and detector hardware may be used for assembling devices and systems of the disclosure for detection capability at large stand-off distances. For example, long stand-off distance irradiation and imaging of detected radiation may be performed using high energy x-ray and/or high energy electrons of about 30 MeV or higher. For experimental testing, surrogate EFPs may be constructed and positioned at various distances from an x-ray source. Detectors such as an SORDS imager which is a combined coded aperture and Compton imager based on NaI detectors may be utilized to image the emitted radiation from a surrogate EFP to demonstrate the identification of an EFP at the maximum stand-off distance possible in the minimum amount of time.

In embodiments where devices, apparatus or system 50 of the disclosure, may be mounted onto vehicle platforms 140, the efficacy and time-to-detect of a real-time detection from safe stand-off distances may be a result of rapid detection and/or identification of a metal source in the shortest time possible and preferably may be in the order of milliseconds to seconds. For example, detection may be in a time of from about fifteen seconds or less.

Speed of detection of a device according to the disclosure may depend on the stand-off distance. For example, when the x-ray generator is nearer the target detection speed may be faster as compared to when an accelerator is further away. In some embodiments, speed of detection achieved by an x-ray generator operable to scan an area suspected of containing a concealed or camouflaged explosive device with high energy x-rays or electrons may be at a rate of from about 1-2 seconds at a stand-off distance of about 10 meters and may be from about 5-10 seconds if the stand-off distance is greater than 75 meters.

Speed of detection may be achieved by sufficient and rapid activation of the liner material, rapid and efficient detection of the resulting emissions (radiation) and analysis, identification and/or decision made by a detector and its output modules in a very short time. In some embodiments, these measurements may be performed at long stand-off distances to afford maximum protection to the hardware and the accompanying personnel.

In some embodiments, the present disclosure also relates to methods for detecting and locating in real-time a concealed or camouflaged explosive device. An example method according to the disclosure is shown in FIG. 2 and may comprise: generating high energy x-rays or electrons; scanning an area suspected of having a concealed or camouflaged explosive device by irradiation of the area with the high-energy x-rays or electrons; activating a metal (or alloy) comprised in the explosive device thereby causing emission of radiation; detecting radiation emitted from the metal.

Another example method according to the disclosure is shown in FIG. 3 and may comprise in addition to the steps of the method set forth in FIG. 2 the steps of optionally and/or additionally identifying the metal (or alloy) by analyzing radiation signatures emitted from the metal; optionally and/or additionally locating the source of radiation to spatially locate the explosive device; and optionally and/or additionally subtracting background radiation from clutter to obtain only radiation signals of interest. One or more of these optional steps may be performed in a method according to the disclosure.

A method as set forth above may also comprise generating and displaying the data generated in a suitable output format such as but not limited to on a computer screen, on a monitor, as a printout and/or as an audible alarm signal.

In some embodiments of the methods of the disclosure, generating high energy x-rays or electrons may comprise using an electron accelerator to generate high energy x-rays. Scanning an area by irradiation of the area by high energy x-rays may comprise bombarding a target area suspected of having a concealed explosive device with high energy x-rays thereby generating radiation from materials in the target area.

Scanning an area with higher energy x-rays and at a faster rate may allow for detection from a greater stand-off distance and/or detection capability at a faster convoy speed. Accordingly, in some embodiments, a method for detecting a concealed explosive device may be performed while moving at convoy speeds of from about 5 miles/hour to about 35 miles/hour.

In some embodiments of the methods, detecting radiation emitted from a target area may involve detecting all radiation emitted from the area and may further involve subtracting background radiation generated by activation of benign clutter materials to obtain radiation signals generated by non-benign materials in the area.

Detection, according to a method of the disclosure, may further involve comparing the radiation signals generated by non-benign materials to radiation signatures of different known materials (including metals, elements, chemicals), that may be located in a databank of radiation signatures and identifying the nature of non-benign material emitting the radiation. Comparing and identifying of radiation signals may be performed by a computer and appropriate software designed to perform such a comparison. Identification of a material emitting radiation allows for identifying the nature of the explosive device. For example, identification of a radiation signature of copper would be interpreted by a computer program as detection of an EFP. Mathematical computer programs may be used to subtract background radiation from radiation data.

As set forth above, in some embodiments, a device or system or method of the disclosure may be able to locate, identify and discriminate point sources of metals of interest (including metal alloys) from ubiquitous background clutter in the field, thereby detecting and locating an explosive device in real-time. For embodiments relating to the speed of detection and/or spatial location of an explosive device, an apparatus, system or method of the disclosure may be operable to: identify and/or quantity spectra of signals of interest (e.g. radiation signatures), generated in a metal of interest (e.g., copper), as a function of source parameters; and/or predict timing and resolution response of detector (e.g., a SORDS imager), based on the identified signals of interest; and/or identify competing signals from benign clutter material and provide methods (e.g., subtraction) to mitigate their effect on detection.

As will be understood by those skilled in the art who have the benefit of the instant disclosure, other equivalent or alternative compositions, devices, methods, and systems for detecting concealed explosive devices such as mines IEDs and EFPs may be envisioned without departing from the description contained herein. Accordingly, the manner of carrying out the disclosure as shown and described is to be construed as illustrative only.

Persons skilled in the art, in light of this disclosure, may make various changes in the shape, size, number, and/or arrangement of parts without departing from the scope of the instant disclosure. For example, a detector as described herein may be comprised of one or more components, modules or detectors based on the detail desired for a particular operation. In addition, the energy and speed of the high-energy x-rays may be scaled up or down to suit the needs and/or desires of a practitioner. An x-ray generator or a detector or an imager may be configured and arranged to be serviceable, interchangeable, and/or replaceable. Also, where ranges have been provided, the disclosed endpoints may be treated as exact and/or approximations as desired or demanded by the particular embodiment. In addition, it may be desirable in some embodiments to mix and match range endpoints.

These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

What is claimed is:

1. An apparatus for real-time detection, identification and location of a concealed or camouflaged explosive device comprising:
   a generator operable to generate high energy x-rays or high energy electrons that are operable to contact and generate radiation from a metal comprised in the concealed or camouflaged explosive device from a stand-off distance, the radiation being generated by activation of atoms in the metal to produce an isotope that emits the radiation;
   a scanner operable to direct the high-energy x-rays or high energy electrons onto a target area suspected of concealing the explosive device; and
   a detector operable to detect radiation generated by the isotope in the metal and determine if the radiation generated by the isotope matches an isotope radiation signature associated with a metal of interest, wherein the metal of interest is a metal that is associated with an explosive device.

2. An apparatus of claim 1, further comprising an output module operable to interface with the detector and display information generated by the detector.

3. The apparatus of claim 1, wherein the stand-off distance is greater than 10 meters.

4. An apparatus of claim 1, wherein the detector is operable to spatially locate the metal.

5. An apparatus of claim 1, wherein the detector is further operable to identify the metal by identifying isotope radiation signatures specific for a respective metal.

6. An apparatus of claim 1, wherein the metal of interest is copper and the isotope radiation signature comprises a 511 keV annihilation photon.

7. An apparatus of claim 1, wherein the metal of interest is copper and the isotope radiation signature comprises photons produced by positron decay of $^{62}Cu$ and $^{64}Cu$.

8. An apparatus of claim 1, wherein the metal of interest is copper and the isotope radiation signature comprises peaks at 875 keV and 1173 keV.

9. An apparatus of claim 1, wherein the metal of interest is iron and the isotope radiation signature comprises a peak at 378 keV.

10. An apparatus of claim 1, wherein the detector is further operable to subtract background radiation emitted from benign clutter in the area being scanned.

11. An apparatus of claim 1, wherein the explosive device is an explosively formed penetrator (EFP), an improvised explosive device (IED) or a land mine.

12. The apparatus of claim 1, wherein the high energy x-rays are Bremsstrahlung x-rays.

13. The apparatus of claim 1, wherein the high energy x-rays are from about 10 MeV to about 20 MeV.

14. An apparatus of claim 1, wherein the apparatus is located in a vehicle, the apparatus further operable to detect and locate the explosive device while the vehicle is moving at a speed of about 5 to about 35 miles per hour.

15. A method for detecting and locating in real-time a concealed or camouflaged explosive device comprising:
   generating high energy x-rays or high energy electrons;
   scanning a target area suspected of having the concealed or camouflaged explosive device with the high energy x-rays or high energy electrons by irradiation of the area from a stand-off distance;
   activating atoms in a metal to produce an isotope causing emission of radiation from the metal comprised in the explosive device by irradiation of the metal with the high energy x-rays or high energy electrons;

detecting radiation emitted from the isotope in the metal;

determining if the radiation emitted by the isotope matches an isotope radiation signature associated with a metal of interest, wherein the metal of interest is a metal that is associated with an explosive device.

16. A method according to claim 15, further comprising identifying the metal by comparing the isotope radiation signature generated from the target area with isotope radiation signatures of known metals.

17. A method according to claim 15, further comprising spatially locating the explosive device by spatially locating the source of radiation in the target area.

18. The method of claim 15, further comprising detecting all radiation emitted from the target area and subtracting background radiation from benign clutter.

19. The method of claim 15, further comprising displaying the information generated by the detector on a display module.

20. The method of claim 15, wherein the detection is performed while moving at convoy speeds.

21. The method of claim 15, wherein scanning comprises using electric and magnetic fields to steer an electron beam in a direction of interest.

22. A system for real-time detection of a concealed or camouflaged explosive device comprising:

a device for generating high energy x-rays or high energy electrons;

a scanner operable to direct the high energy x-rays or high energy electrons to irradiate an area suspected of containing an explosive device;

a detector operable to detect radiation generated by an isotope produced by activation of atoms in a metal in response to irradiation by the high energy x-rays or high energy electrons;

the detector further operable to determine if the radiation generated by the isotope matches an isotope radiation signature associated with a metal of interest, wherein a metal of interest is a metal comprised in an explosive device;

a detector component operable to identify the explosive device by comparing the radiation generated by the isotope to a database of isotope radiation signatures of known metals of interest;

a sensor operable to locate the source of the radiation and thereby identify the spatial location of the explosive device;

a module operable to interface with the detector and display the information generated; and optionally an alarm module operable to activate upon detection of a metal and alert an operator of the presence of the explosive device.

* * * * *